United States Patent
Zicker et al.

(10) Patent No.: US 8,492,432 B2
(45) Date of Patent: Jul. 23, 2013

(54) METHODS FOR THE TREATMENT OF KIDNEY DISEASE

(75) Inventors: Steven Curtis Zicker, Lawrence, KS (US); Karen Joy Wedekind Lake, St. Louis, MO (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 410 days.

(21) Appl. No.: 12/063,703

(22) PCT Filed: Aug. 17, 2006

(86) PCT No.: PCT/US2006/032126
§ 371 (c)(1),
(2), (4) Date: Feb. 13, 2008

(87) PCT Pub. No.: WO2007/022344
PCT Pub. Date: Feb. 22, 2007

(65) Prior Publication Data
US 2008/0214653 A1 Sep. 4, 2008

Related U.S. Application Data

(60) Provisional application No. 60/709,071, filed on Aug. 17, 2005.

(51) Int. Cl.
*A61K 31/355* (2006.01)
*A61K 31/34* (2006.01)

(52) U.S. Cl.
USPC ..................................... 514/458; 514/474

(58) Field of Classification Search
USPC .................................. 514/458, 474
See application file for complete search history.

(56) References Cited

U.S. PATENT DOCUMENTS

| | | | |
|---|---|---|---|
| 3,997,675 A | 12/1976 | Eichelburg | |
| 4,898,890 A | 2/1990 | Sato et al. | |
| 5,292,538 A | 3/1994 | Paul et al. | |
| 5,339,771 A | 8/1994 | Axelrod | |
| 5,419,283 A | 5/1995 | Leo | |
| 5,496,545 A | 3/1996 | Holmes-Farley et al. | |
| 5,621,117 A | 4/1997 | Bethge et al. | |
| 5,723,441 A | 3/1998 | Higley et al. | |
| 5,858,024 A * | 1/1999 | De Lacharriere et al. | 8/408 |
| 5,916,912 A | 6/1999 | Ames et al. | |
| 5,976,568 A | 11/1999 | Riley | |
| 6,194,454 B1 | 2/2001 | Dow | |
| 6,228,418 B1 | 5/2001 | Gluck et al. | |
| 6,306,392 B1 | 10/2001 | Cavazza | |
| 6,426,362 B1 | 7/2002 | Miller et al. | |
| 6,447,989 B1 | 9/2002 | Comper | |
| 6,458,767 B1 | 10/2002 | Murphy-Ullrich et al. | |
| 6,492,325 B1 | 12/2002 | Cosgrove | |
| 6,589,748 B2 | 7/2003 | Comper | |
| 6,599,876 B2 | 7/2003 | Kojima | |
| 6,784,159 B2 | 8/2004 | Holub et al. | |
| 2001/0043983 A1 * | 11/2001 | Hamilton | 426/635 |
| 2002/0025310 A1 | 2/2002 | Bland | |
| 2002/0028762 A1 | 3/2002 | Kojima | |
| 2003/0060503 A1 | 3/2003 | Hamilton | |
| 2003/0190343 A1 | 10/2003 | Thombre et al. | |
| 2003/0198661 A1 | 10/2003 | Harper et al. | |
| 2003/0224061 A1 | 12/2003 | Pacioretty et al. | |
| 2004/0047896 A1 | 3/2004 | Malnoe et al. | |
| 2004/0137080 A1 | 7/2004 | Cremisi | |
| 2005/0026225 A1 | 2/2005 | Comper | |
| 2005/0123628 A1 | 6/2005 | Zabrecky | |
| 2005/0192352 A1 | 9/2005 | Caterson et al. | |
| 2005/0222050 A1 | 10/2005 | Pan | |
| 2006/0134014 A1 | 6/2006 | Scherl et al. | |
| 2006/0263344 A1 | 11/2006 | Skop et al. | |
| 2006/0270625 A1 | 11/2006 | Vinik et al. | |
| 2008/0299286 A1 | 12/2008 | Josephson et al. | |
| 2009/0004299 A1 * | 1/2009 | Wedekind et al. | 424/725 |
| 2009/0149529 A1 | 6/2009 | Zicker et al. | |
| 2009/0155393 A1 * | 6/2009 | Zicker et al. | 424/736 |
| 2009/0156658 A1 | 6/2009 | Zicker et al. | |
| 2009/0182032 A1 | 7/2009 | Zicker et al. | |

FOREIGN PATENT DOCUMENTS

| | | |
|---|---|---|
| CN | 1578627 A | 2/2005 |
| DE | 19818563 | 10/1999 |
| EP | 1118332 | 7/2001 |
| EP | 1247456 | 10/2002 |
| JP | H11-246398 | 9/1999 |

(Continued)

OTHER PUBLICATIONS

Ikeda-Douglass et al., "Prior Experience, Antioxidants, and Mitochondrial Cofactors Improve Cognitive Function in Aged Beagles", Veterinary Therapeutics, vol. 5, No. 1, pp. 5-17 (Spring 2004).*

(Continued)

*Primary Examiner* — Kevin E Weddington
(74) *Attorney, Agent, or Firm* — Thomas Hunter

(57) ABSTRACT

The invention provides compositions for preventing or treating kidney disease and improving kidney function comprising at least two ingredients selected from the group consisting of antioxidants and mitochondrial cofactors in amounts sufficient for preventing or treating kidney disease or for improving kidney function and methods for preventing and treating kidney disease or improving kidney function comprising administering such compositions to an animal susceptible to or suffering from kidney disease or impaired kidney function. In a preferred embodiment, the composition is admixed with one or more food ingredients to produce a food composition useful for preventing or treating kidney disease and improving kidney function, particularly in senior animals.

18 Claims, No Drawings

FOREIGN PATENT DOCUMENTS

| | | |
|---|---|---|
| RU | 2324364 | 5/2008 |
| RU | 2341259 | 12/2008 |
| WO | WO 00/44375 | 8/2000 |
| WO | WO 01/07039 | 2/2001 |
| WO | WO 01/58271 | 8/2001 |
| WO | WO 02/26221 | 4/2002 |
| WO | WO 02/35943 | 5/2002 |
| WO | WO 2004/113570 A2 | 12/2004 |
| WO | WO 2005/006877 | 1/2005 |
| WO | WO 2005/041999 | 5/2005 |
| WO | WO 2006/042728 | 4/2006 |
| WO | WO 2006/053010 | 5/2006 |
| WO | WO 2006/058248 | 6/2006 |
| WO | WO 2006/071952 | 7/2006 |
| WO | WO 2006/074089 | 7/2006 |
| WO | WO 2006/113752 | 10/2006 |

OTHER PUBLICATIONS

Siwak et al., "Chronic antioxidant and mitochondrial cofactor administration improves discrimination learning in aged but not young dogs", Progress in Neuro-Psychopharmacology & Biological Psychiatry, Vo. 29, pp. 461-469 (Feb. 2005).*
Asghar, M. "Antioxidant Supplementation Normalizes Elevated Protein Kinase C Activity in the Proximal Tubules of Old Rats" Soc for Exp Bio & Med (2004) pp. 270-275.
Cutler, R.G. "Antioxidants and Aging" Am J Clin Nutr (1991) 53:373S-379S.
Chiba Y. et al. "The protective effects of taurine against renal damage by salt loading in Dahl salt-sensitive rats" Journal of Hypertension (2002) 20:2269-2274.
Beckman, K.B. "The Free Radical Theory of Aging Matures" American Physiological Society (1998) 78:2 pp. 547-581.
Craven, P.A. et al. "Effects of Supplementation with Vitamin C or E on Albuminuria, Glomerular TGF-B, and Glomerular Size in Diabetes" American Society of Nephrology (1997).
Kealy, R.D. et al. "Effects of diet restriction on life span and age related changes in dogs" JAVMA (2002) 220:9 pp. 13151320.
Kornatowska, K et al, "Effect of Vitamin E and Vitamin C Supplementation on Antioxidative State and Renal Glomerular Basement Membrane Thickness in Diabetic Kidney" (2003).
Lee, C et al. "The Impact of a-Lipoic Acid, Coenzyme Q10, & Caloric Restriction on Life Span and Gene Expression Patterns in Mice" Free Rad Bio & Med (2004) 36:8 pp. 1043-1057.
Luft, F. "Microalbuminuria and essential hypertension: renal and cardiovascular implications" Nephrology & Hypertension (1997) 6:553-557.
Trachtman, H. et al. "Taurine attenuates renal disease in chronic puromycin aminonuculeoside nephropathy" American Physiological Soc (1992) pp. F117-F123.
Tylicki, L et al. "Antioxidants: A Possible Role in Kidney Protection" Kidney Blood Pressure Res (2003) 26:303-314.
Van Den Branden, C. et al. "Vitamin E Protects Renal Antioxidant Enzymes and Attentuatees Glomerulosclerosis in Adriamycin-Treated Rats" Nephron (2002) 91:129-133.
Villeponteau, B. "Nutraceutical Interventions May Delay Aging and the age-related diseases" Experimental Gerontology (2000) pp. 1405-1471.
Goetz F., et al. "Induced Precipitation of Calcium-oxalate Crystals and its Prevention in Labaoratory Animals" Intnl Urology & Nephrology (1986) 18:4 pp. 363-368.
Melhem, M. et al. "Effects of dietary Supplementation of x-Lipoic Acid on Early Glomerular Injury in diabetes Mellitus" J Am Soc Nephrol (2001) 12: pp. 124-133.
Tractman, H. "Dietary Vitamin E Supplementation Ameliorates Renal Injury in Chronic Puromycin Aminoncleoside Nephropathy" J Am Soc Nephrol (1995) 5:1811-1819.
Manning R. Davis et al. "Oxidative Stress and Antioxidant Treatment in Hypertension and the Associated Renal Damage," Am J Nephrol (2005) pp. 311-317 vol. 25.
Tian, Niu et al. "Antioxidant Treatment Prevents Renal Damage and Dysfunction and Reduces Arterial Pressure in Salt-Sensitive Hypertension," Hypertension Journal of the American Heart Association, (2005) pp. 934-939 vol. 45.
Asghar et al., "Antioxidant Supplementation Normalizes Elevated Protein Kinase C Activity in the Proximal Tubules of Old Rats," Soc. For Exp. Bio & Med, pp. 270-275, vol. 229 (2004).
Hasselwander et al., "Oxidative Stress in Chronic Renal Failure," Free Rad. Res. 29:1-11 (1998).
Kopple et al., "L-carnitine Ameliorates Gentamicin-induced Renal Injury in Rats," Nephrology Dialysis Transplantation, vol. 17, No. 2, pp. 2122-21231 (2002).
Ongajooth et al., "Role of Lipid Peroxidation, Trace Elements and Antioxidant Enzymes in Chronic Renal Disease Patients," J. Med. Assoc. Thai., 79:791-800 (1996).
Shah, S., "The Role of Reactive Oxygen Metabolites in Glomerular Disease," Annu. Rev. Physiol., 57:245-62 (1995).
Amudha et al., 2007, "Protective Effect of Lipoic Acid on Oxidative and Peroxidative Damage in Cyclosporine A-Induced Renal Toxicity," Int. Immunopharmacology 7(11):1442-1449.
International Search Report and Written Opinion in International Application No. PCT/US09/069679, mailed Apr. 7, 2010.
Lexis et al., 2006, "Alpha-Tocopherol and Alpha-Lipoic Acid Enhance the Erythrocyte Antioxidant Defence in Cyclosporine A-Treated Rats," Basic & Clinical Pharmacol. & Toxicol. 98(1):68-73.
Loftin et al., 2009, "Therapy and Outcome of Suspected Alpha Lipoic Acid Toxicity in Two Dogs," J. Vet. Emergency and Critical Care 19(5):501-506.
"Dysgeusia," Encyclopedia Article, downloaded from www.absoluteastronomy.com/topics/Dysgeusia, dated Sep. 7, 2008, 5 pages.
Chen et al., 1995, "Vitamin E, Selenium, Trolox C, Ascorbic Acid Palmitate, Acetylcysteine, Coenzyme Q, B-Carotene, Canthaxanthin, and (+)-Catechin Protect Against Oxidative Damage to Kidney, Heart, Lung and Spleen," Free Radical Research 22(2):177-186.
Markova et al., 2001, Pharmacology pp. 285-286.
Qiong et al., 2007, "New Feed Additive—Lipoic Acid," Animals Breeding and Feed 7:56-58.
Welge-Lussen, Review Article, "Re-establishment of olfactory and taste functions," downloaded from www.egms.de/en/journals/cto/2005-4/cto000012.shtml. Dated Sep. 28, 2005.

* cited by examiner

METHODS FOR THE TREATMENT OF KIDNEY DISEASE

This application claims priority to U.S. Provisional Application Ser. No. 60/709,071 filed Aug. 17, 2005, the disclosure of which is incorporated herein by reference.

BACKGROUND OF THE INVENTION

1. Field of the Invention

This invention relates generally to compositions and methods for combating kidney disease and improving kidney function and particularly to the use of food compositions for preventing and treating kidney disease and improving kidney function.

2. Description of the Prior Art

It has been postulated since 1956 that the production of active oxygen species or free radicals during aerobic respiration results in oxidative damage that hastens aging and death in animals (Beckman, K., et al., "The Free Radical Theory of Aging Matures," Phys. Rev., 78: 547-581 (1998)). Active oxygen species cause aging through various mechanisms, including directly damaging cellular DNA (Cutler, R., "Antioxidants and aging", Am. J. Clin. Nutr., 53: 373S-379S (1991) and lipids and proteins (Tylicki, L., et al. "Antioxidants: A Possible Role in Kidney Protection," Kid. Bl. Press. Res., 26: 303-314 (2003)). Free radicals, often produced in the mitochondria, where aerobic respiration occurs, damage mitochondrial DNA, proteins, and lipids, e.g., U.S. Patent App. Pub. No. US 2003/0060503.

It has also been postulated that active oxygen species may play a role in causing kidney disease (Ongajooth L., et al. "Role of Lipid Peroxidation, Trace Elements and Antioxidant Enzymes in Chronic Renal Disease Patients," J. Med. Assc. That., 79:791-800 (1996)). Several mechanisms have been proposed to account for this increase in renal failure, e.g., Hasselwander, et al. "Oxidative Stress in Chronic Renal Failure," Free Rad. Res. 29:1-11 (1998); Shah, S., "The Role of Reactive Oxygen Metabolites in Glomerular Disease," Annu. Rev. Physiol., 57:245-62 (1995)), but scientific studies to date are inconclusive regarding whether antioxidant treatment is beneficial to those with kidney disease. Some studies indicate that there is a role for various antioxidant supplementations in the protection against kidney disease, e.g., Kedziora-Komatowska et al, "Effect of Vitamin E and Vitamin C Supplementation on Antioxidative State and Renal Glomerular Basement Membrane Thickness in Diabetic Kidney", Nephron Exp. Nephrol., 95:e134-e143 (2003). Other studies note the potential pro-oxidant properties of antioxidant supplements, concluding that there is not yet enough experimental evidence to recommend antioxidant supplements to alleviate kidney disease, e.g., Tylicki.

However, despite years of studies and developments relating to kidney disease and renal function, kidney disease and poor renal function remain a major health problem. There is, therefore, a need for new methods and compositions for preventing and treating kidney disease and for improving kidney function.

SUMMARY OF THE INVENTION

It is, therefore, an object of the present invention to provide compositions and methods for preventing and treating kidney disease.

It is another object of the present invention to provide compositions and methods for improving kidney function.

It is a further object of the invention to provide methods for preventing and treating kidney disease and for improving kidney function in senior animals.

It is another object of the invention to provide food compositions for preventing and treating kidney disease.

It is another object of the invention to provide articles of manufacture in the form of kits that contain combinations of compositions and devices useful for preventing and treating kidney disease.

It is a further object of the invention to decrease the morbidity and mortality caused by kidney disease.

These and other objects are achieved using a novel compositions and methods for preventing or treating kidney disease and for improving kidney function. The compositions comprise at least two ingredients selected from the group consisting of antioxidants and mitochondrial cofactors in amounts sufficient for preventing or treating kidney disease or to improve kidney function. Food compositions comprising one or more food ingredients and the compositions are preferred. The methods comprise administering such compositions to animals susceptible to or suffering from kidney disease or administering the compositions to animals experiencing a decline in kidney function, particularly a decline due to aging. Kits comprising the composition components (at least two of an antioxidant and/or mitochondrial cofactor) and one or more optional feed ingredients and renal drugs are also provided.

Other and further objects, features and advantages of the present invention will be readily apparent to those skilled in the art.

DETAILED DESCRIPTION OF THE INVENTION

Definitions

The term "animal" means a human or other animal likely to develop or suffering from kidney disease or a decline in kidney function (particularly due to aging), including avian, bovine, canine, equine, feline, hicrine, murine, ovine, and porcine animals. Preferably, the animal is a canine or feline.

The term "renal drug" means any compound, composition, or drug useful for preventing or treating kidney disease.

The term "in conjunction" means that one or more of the compositions and compounds (e.g. renal drugs or composition components) of the present invention are administered to an animal (1) together in a food composition or (2) separately at the same or different frequency using the same or different administration routes at about the same time or periodically. "Periodically" means that the compositions, food compositions, and compounds are administered on a dosage schedule acceptable for a specific composition, food composition, and compound and that the food compositions are administered or fed to an animal routinely as appropriate for the particular animal. "About the same time" generally means that the compositions, composition components, renal drugs, and food compositions are administered at the same time or within about 72 hours of each other. In conjunction specifically includes administration schemes wherein renal drugs are administered for a prescribed period and the compositions are administered indefinitely.

The term "companion animal" means an individual animal of any species kept by a human caregiver as a pet or any individual animal of a variety of species that have been widely domesticated as pets, including dogs (*Canis familiaris*) and cats (*Felis domesticus*), whether or not the individual animal is kept solely or partly for companionship.

The term "senior" refers to a life-stage of an animal. For small and regular breed canines, as well as for felines, the "senior" stage starts at about age 7. For large breed canines (a canine that weighs more than 50 pounds (22.7 kg) as an adult), the "senior" stage starts at about age 5.

The term "improve kidney function" means that a composition is administered to or a method is used for an animal for a period effective to improve kidney function as determined by comparison with kidney function in animals not being administered the composition or using the method.

The term "antioxidant" means a substance capable of reacting with and neutralizing free radicals. Examples of such substances include beta-carotene, selenium, coenzyme Q10 (ubiquinone), lutein, tocotrienols, soy isoflavones, S-adenosylmethionine, glutathione, N-acetylcysteine, vitamin E, vitamin C, and α-lipoic acid. Examples of foods containing useful levels of one or more antioxidants include but are not limited to ginkgo biloba, green tea, broccoli, citrus pulp, grape pomace, tomato pomace, carrot, spinach, and a wide variety of fruit and vegetable meals.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "a host cell" includes a plurality of such host cells.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent application, and publications mentioned herein are incorporated herein by reference to the extent allowed by law for the purpose of describing and disclosing the compounds and methodologies reported therein that might be used with the present invention. However, nothing herein is to be construed as an admission that the invention is not entitled to antedate such disclosure by virtue of prior invention.

The Invention

In one aspect, the present invention provides a composition for preventing and treating kidney disease and for improving kidney function. The composition comprises at least two ingredients selected from the group consisting of antioxidants and mitochondrial cofactors in amounts sufficient for preventing or treating kidney disease or for improving kidney function. The invention is based upon the novel discovery that kidney function can be altered by administering the composition to an animal and that altering kidney function with the composition can prevent or treat kidney disease and can improve kidney function, particularly in senior animals. Without being bound by theory, it is believed that composition if effective in preventing and treating kidney disease because it reduces oxidative stress in an animal.

The composition comprises at least about 100 ppm of one or more antioxidants and/or at least about 25 ppm of one or more mitochondrial cofactors. The compositions contain antioxidants and mitochondrial cofactors in amounts that are not deleterious to an animal's health, e.g., amounts that do not cause undesirable toxic effects in the animal. In certain embodiments, the composition comprises at least one ingredient that is an antioxidant and at least one ingredient that is a mitochondrial cofactor.

Suitable antioxidants and mitochondrial cofactors for use in the compositions and methods of the present invention include, but are not limited to, vitamin E, L-carnitine, α-lipoic acid, and vitamin C. Vitamin E can be in any form suitable for consumption by an animal including, but not limited to, any tocopherol or tocotrienol compound, any enantiomer or racemate thereof, and any mixture of such compounds having vitamin E activity. Vitamin E can be administered as any one or a mixture of different forms or in the form of various derivatives thereof such as esters, including vitamin E acetate, succinate, palmitate and the like, that exhibit vitamin E activity after ingestion by an animal. L-carnitine can be administered as such or in the form of any of various derivatives of carnitine, such as salts, e.g., hydrochloride, fumarate and succinate salts, acetylated carnitine, and the like. α-Lipoic acid can be administered as such, as a lipoate derivative, for example as described in U.S. Pat. No. 5,621,117, or as a racemic mixture, salt, ester or amide thereof. In one embodiment DL-α-lipoic acid is used. Vitamin C can be administered as ascorbic acid, for example L-ascorbic acid, or as various derivatives thereof such as calcium phosphate salt, cholesteryl salt, and ascorbate-2-monophosphate. Salts of vitamin C include, for example, sodium salt, calcium salt, zinc salt and ferrous salt. Esters include, for example, stearate, palmitate and like derivatives. Vitamin C or a derivative thereof can be in any physical form, for example, a liquid, a semisolid, a solid, or a heat stable form that exhibits vitamin C activity after ingestion by the animal. In various embodiments, the composition comprises at least two, at least three, or all four of vitamin E, vitamin C, L-carnitine and α-lipoic acid.

In another aspect, the present invention provides a food composition for preventing and treating kidney disease and/or for improving kidney function. The food composition comprises one or more food ingredients admixed with antioxidants and mitochondrial cofactors in amounts sufficient for preventing or treating kidney disease or for improving kidney function. Generally, the food composition comprises one or more food ingredients and at least about 100 ppm of one or more antioxidants and/or at least about 25 ppm of one or more mitochondrial cofactors. In some embodiments, the food composition comprises one or more food ingredients and the antioxidants and mitochondrial cofactors in amounts of at least about 500 ppm vitamin E, at least about 40 ppm vitamin C, at least about 100 ppm L-carnitine, and at least about 25 ppm α-lipoic acid. Preferably, the composition comprises one or more food ingredients and from about 500 to about 1500 ppm vitamin E, from about 40 to about 150 ppm vitamin C, from about 125 to about 400 ppm L-carnitine, and from about 25 to about 200 ppm α-lipoic acid. In a feline food, the concentration of α-lipoic acid, if present, is at least about 25 ppm. In a canine food, the concentration of α-lipoic acid, if present, is at least about 50 ppm. In one embodiment, the food composition further comprises at least about 1% by weight of at least one of tomato pomace, dried spinach, dried carrot, dried citrus pulp, and dried grape pomace.

In certain embodiments, the food composition comprises one or more food ingredients admixed with at least one ingredient that is an antioxidant and at least one ingredient that is a mitochondrial cofactor.

The food ingredients useful in the present invention include any food ingredient suitable for consumption by an animal. Typical food ingredients include but are not limited to fats, carbohydrates, proteins, fibers, nutritional balancing agents such as vitamins, minerals, and trace elements, and mixtures thereof. Skilled artisans can select the amount and type of food ingredients for a typical food based upon the dietary requirements of the animal, e.g., the animal's species, age, size, weight, health, and function.

The food ingredient part of the food composition can comprise 100% of any particular food ingredient of can comprise a mixture of food ingredients in various proportions. In preferred embodiments, the food composition comprises a combination of food ingredients in amounts from about 0% to about 50% fat, from about 0% to about 75% carbohydrate, from about 0% to about 95% protein, from about 0% to about 40% dietary fiber, and from about 0% to about 15% of one or more nutritional balancing agents.

The fat and carbohydrate food ingredient is obtained from a variety of sources such as animal fat, fish oil, vegetable oil, meat, meat by-products, grains, other animal or plant sources, and mixtures thereof. Grains include wheat, corn, barley, and rice.

The protein food ingredient is obtained from a variety sources such as plants, animals, or both. Animal protein includes meat, meat by-products, dairy, and eggs. Meats include the flesh from poultry, fish, and animals such as cattle, swine, sheep, goats, and the like. eat by-products include lungs, kidneys, brain, livers, stomachs, and intestines. The protein food ingredient may also be free amino acids and/or peptides. Preferably, the protein food ingredient comprises meat, a meat by-product, dairy products, or eggs.

The fiber food ingredient is obtained from a variety of sources such as vegetable fiber sources, e.g., cellulose, beet pulp, peanut hulls, and soy fiber.

The nutritional balancing agents are obtained from a variety of sources known to skilled artisans. e.g., vitamin and mineral supplements and food ingredients. Vitamins and minerals can be included in amounts required to avoid deficiency and maintain health. These amounts are readily available in the art. The National Research Council (NRC) provides recommended amounts of such nutrients for farm animals. See, e.g., Nutrient Requirements of Swine (10th Rev. Ed., Nat'l Academy Press, Wash. D.C., 1998), Nutrient Requirements of Poultry (9th Rev. Ed., Nat'l Academy Press, Wash. D.C., 1994), Nutrient Requirements of Horses (5th Rev. Ed., Nat'l Academy Press, Wash. D.C., 1989). The American Feed Control Officials (AAFCO) provides recommended amounts of such nutrients for dogs and cats. See American Feed Control Officials, Inc., Official publication, pp. 129-137 (2004). Vitamins generally useful as food additives include vitamin A, vitamin B1, vitamin B2, vitamin B6, vitamin B12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

The compositions and food compositions may contain additions ingredients such as vitamins, minerals, fillers, palatability enhancers, binding agents, flavors, stabilizers, emulsifiers, sweeteners, colorants, buffers, salts, coatings, and the like known to skilled artisans. Stabilizers include substances that tend to increase the shelf life of the composition such as preservatives, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches. Specific amounts for each composition component, food ingredient, and other ingredients will depend on a variety of factors such as the particular components and ingredients included in the composition; the species of animal; the animal's age, body weight, general health, sex, and diet; the animal's consumption rate; the type of kidney disease being treated; and the like. Therefore, the component and ingredient amounts may vary widely and may deviate from the preferred proportions described herein.

Food compositions may be prepared in a canned or wet form using conventional food preparation processes known to skilled artisans. Typically, ground animal proteinaceous tissues are mixed with the other ingredients such as fish oils, cereal grains, balancing ingredients, special purpose additives (e.g., vitamin and mineral mixtures, inorganic salts, cellulose and beet pulp, bulking agents, and the like) and water in amounts sufficient for processing. These ingredients are mixed in a vessel suitable for heating while blending the components. Heating of the mixture is effected using any suitable manner, e.g., direct steam injection or using a vessel fitted with a heat exchanger. Following the addition of the last ingredient, the mixture is heated to a temperature of from about 50° F. to about 212° F. Temperatures outside this range are acceptable but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. Sterilization is usually accomplished by heating to temperatures of greater than about 230° F. for an appropriate time depending on the temperature used, the composition, and similar factors. The compositions of the present invention can be added to the food compositions before, during, or after preparation.

Food compositions may be prepared in a dry form using conventional processes known to skilled artisans. Typically, dry ingredients such as animal protein, plant protein, grains, and the like are ground and mixed together. Moist or liquid ingredients, including fats, oils, animal protein, water, and the like are then added to and mixed with the dry mix. The mixture is then processed into kibbles or similar dry pieces. Kibble is often formed using an extrusion process in which the mixture of dry and wet ingredients is subjected to mechanical work at a high pressure and temperature and forced through small openings and cut off into kibble by a rotating knife. The wet kibble is then dried and optionally coated with one or more topical coatings such as flavors, fats, oils, powders, and the like. Kibble also can be made from the dough using a baking process, rather than extrusion, wherein the dough is placed into a mold before thy-heat processing. The food compositions can be in the form of a treat using an extrusion or baking process similar to those described above for dry food or a toy such as those disclosed in U.S. Pat. Nos. 5,339,771 and 5,419,283. The compositions of the present invention can be added to the food compositions before, during, or after preparation.

Treats include compositions that are given to an animal to entice the animal to eat during a non-meal time, e.g., dog bones for canines. Treats may be nutritional wherein the composition comprises one or more nutrients or and may have a food-like composition. Non-nutritional treats encompass any other treats that are non-toxic. The composition or components are coated onto the treat, incorporated into the treat, or both. Treats of the present invention can be prepared by an extrusion or baking process similar to those used for dry food. Other processes also may be used to either coat the composition on the exterior of existing treat forms or inject the composition into an existing treat form.

All weights and concentrations for the compositions of the present invention are based on dry weight of a composition after all components and ingredients are admixed.

In another aspect, the present invention provides the compositions and food compositions of the present invention further comprising one or more renal drugs. Renal drugs useful in the invention are any renal drugs known to skilled artisans to be useful for combating kidney disease. Preferred drugs include lysosome-activating compounds such as those described in U.S. Pat. No. 6,589,748, triterpene saponins such as those described in U.S. Pat. No. 6,784,159, activin inhibitors such as those described in U.S. Pat. No. 6,599,876 and US Patent Application Number (USPAN) 20020028762, integrin receptor inhibitors and TGF inhibitors such as those described in U.S. Pat. No. 6,492,325, TGF activation inhibitors such as those described in U.S. Pat. No. 6,458,767, and insulin-like growth factor (IGF) as described in U.S. Pat. No. 5,723,441. Most Preferred drugs include Converting Enzyme (ACE) inhibitors, androgens, erythropoiten, and calcitriol. Angiotensin and endothelin are potent systemic vasoconstrictors with specific intrarenal effects that contribute to progressive renal injury. A variety of renal drugs are used to mitigate the effect of these vasoconstrictors. Angiotensin converting enzyme inhibitors (enalapril—Enacard and Vasotec and benazepril—Lotensin) have been associated with a reduction in the severity of proteinuria and slowing of progression of renal failure. The ACE inhibitor enalapril (Enacard, Vasotec) limits glomerular and systemic hypertension, proteinuria, and glomerular and tubulointerstitial lesions. Angiotensin blockers and endothelin inhibitors have beneficial effects in renal disease. Vasopeptide inhibitors are agents that inhibit both ACE and neutral endopeptidase, an enzyme involved in the breakdown of natriuretic peptides, adrenomedullin, and bradykinin. These renal drugs decrease angiotenin II production and increase accumulation of vasodilators. Renal animals with systemic hypertension respond to calcium channel blockers such as amlodipine (Norvasc). Uremic gastritis (esophagitis, gastritis, gastric ulceration and hemorrhage) is treated with H2 receptor antagonists (cimetidine—Tagamet, famotidine—Pepcid), proton pump blockers (omeprazole—Prilosec), cytoprotective agents (misoprostol—Cytotec), and antiemetic drugs that effect the emetic center (chlorpromazine—Thorazine, perchlorperazine—Compazine, metoclopramide—Reglan). Androgens or anabolic steroids (Stanozol, Winstrol-V) are used in the treatment of anemia associated with chronic renal failure. Hormone replacement therapy using recombinant human (or other species) erythropoiten (Epoetin alpha, Epogen, Procrit) is the treatment of choice for severe anemia associated with renal failure. Phosphate binders (aluminum hydroxide—Amphojel, aluminum carbonate—Basaljel) are used to control hyperphosphatemia and secondary renal hyperparathyroidism. Calcitriol (1, 25-dihydroxycholecalciferol) (Rocaltrol) and vitamin D analogues cause a calcium-independent suppression of parathyroid hormone (PTH). Administration of phosphate binders, calcitriol and related compounds has been advocated in chronic renal failure to prevent multi-system toxicity caused by PTH. Potassium depletion and hypokalemia are common in cats with chronic renal failure. Oral supplementation of potassium in the form of potassium gluconate (Tumil K, RenaKare, Kolyum) or citrate is recommended. Holistic renal drugs and compositions are also included in the present invention. Preferred holistic renal drugs include cranberry extract and mannose. Cranberry extract is purported to reduce the prevalence of urinary tract infection which is a common risk factor for long-term decline of renal function. Renal drugs include typical small molecule pharmaceuticals, small proteins, macromolecular proteins and molecules, and antibodies and further include vaccines designed to prevent renal disease. Antibodies include polyclonal and monoclonal antibodies and immunoglobulin fragments such as Fv, Fab, Fab', F(ab')2, or other antigen-binding antibody subsequences that interact with an antigen and perform the same biological function as a native antibody. The renal drugs are administered to the animal using any method appropriate for the renal drug and in amounts known to skilled artisans to be sufficient to treat or prevent renal disease.

In a further aspect, the present invention provides methods for preventing and treating kidney disease and/or for improving kidney function. One method comprises administering in conjunction a kidney disease preventing or treating amount of a composition comprising at least two ingredients selected from the group consisting of antioxidants and mitochondrial cofactors. The method is particularly applicable to animals that are susceptible or suffering from kidney disease caused by aging, xenobiotics, or pathogens. In another aspect, the invention provides methods for improving kidney function by administering a kidney function improving amount of the composition to an animal. The method is particularly applicable to aging and senior animals that are experiencing a decline in kidney function due to aging. Other methods for accomplishing these aspects of the invention comprise administering the composition in conjunction with a food composition comprising one or more food ingredients. In a preferred embodiment, the composition and the food ingredients are administered in a food composition comprising an admixture of the composition and the food ingredients. In preferred embodiments, the animal is a feline or a canine. In one embodiment, the animal is a companion animal such as working dogs, farm cats kept for rodent control, pet dogs, and pet cats. In another embodiment, the animal is a senior animal. In certain embodiments, the methods comprise administering to the animal a composition wherein at least one ingredient is an antioxidant and at least one ingredient is a mitochondrial cofactor. The methods are beneficial for decreasing the amount of albumin in the urine of senior and other animals. A moderate increase in albumin in the urine, or microalbuminuria, is considered to be an early indicator of renal glomerular disease. Without being bound by any particular theory, it is believed that the benefits described above result from physiological effects of the addition of antioxidants and/or mitochondrial cofactors to animal diets, particularly senior animal diets, and that these effects are related to mitigation of the production of, and the damage caused by, toxic free radicals. The methods slow, arrest, or reverse age-related decline in kidney function. Such effects are considered to improve kidney function.

In one embodiment, the method comprises administering to an animal, particularly a senior animal, a food composition comprising at least about 500 ppm, for example about 500 to about 1500 ppm, vitamin E; at least about 100 ppm, for example about 125 to about 400 ppm, L-carnitine; at least about 25 ppm, for example about 25 to about 200 ppm, α-lipoic acid; and at least about 40 ppm, for example about 40 to about 150 ppm, vitamin C. Such a composition optionally further comprises at least about 1% by weight of at least one of tomato pomace, dried spinach, dried carrot, dried citrus pulp, and dried grape pomace.

The compositions are administered to the animal using any suitable method, preferably by feeding the compositions to the animal.

The methods are accomplished by administering the compositions to the animal in various forms. For example, one or more composition components and food ingredients are in separate containers and admixed just prior to administration. In one embodiment, the antioxidants and mitochondrial cofactors are admixed in one container and the resulting composition mixed with food ingredients just prior to administration, e.g., by stirring the composition into or sprinkling the composition onto the food ingredients. In another, one or more of the composition components are admixed with the food ingredients during manufacture and the remaining composition components admixed with such food ingredients just prior to administration. In a further, the composition is a component of a pour-on formulation (preferably containing vitamins and minerals) that is applied to food ingredients prior to administration. In another, the composition is admixed with one or more food ingredients and such admixture is mixed with other food ingredients before administration. In a further, the composition is coated onto the food ingredients during the manufacturing process or after the food composition is manufactured. In another, the composition is administered orally and the food composition is fed to the animal.

The composition is administered orally using any suitable form for oral administration, e.g., tablets, pills, suspensions, solutions (possibly admixed with drinking water), emulsions, capsules, powders, syrups, and palatable feed compositions (a confectionery for a human or a treat or flavored treat for an animal). In a preferred embodiment, the composition components and the food ingredients are admixed during manufacture process used to prepare the food composition suitable for administration in the form of a food for consumption by the animal.

A further method comprises administering the composition or food composition of the present invention in conjunction with one or more renal drugs. Typically, health care professionals, e.g., doctors and veterinarians, diagnose kidney disease in an animal and prescribe a renal drug (any drug useful to prevent or treat kidney disease in an animal) to treat the disease. The animal is administered the renal drug until the symptoms cease and the disease is considered cured. Generally, the renal drug is not administered after the disease is considered cured. Administration of the renal drug is resumed only if the animal has a reoccurrence of the kidney disease. In the present invention, the compositions and renal drugs are administered in conjunction to the animal during treatment. After administration of the renal drug ceases, the compositions are administered to the animal to prevent reoccurrence of the disease. In another embodiment, the compositions are administered to the animal only after use of the renal drug is discontinued to prevent disease reoccurrence.

Any suitable diagnostic method of assessing kidney function can be used to determine whether an improvement occurs. In one embodiment, kidney function is assessed by the level(s) of one or more biomarkers in a tissue or biofluid sample. A particularly useful diagnostic method herein comprises measurement of albumin content of urine. Elevated albumin levels in urine, in particular the slightly to moderately elevated levels known as microalbuminuria, are an indicator of a decline in kidney function as occurs, for example, in incipient kidney disease.

In a further aspect, the present invention provides a kit for administering a kidney disease preventing or treating amount of a composition or a kidney function improving amount of a composition to an animal comprising in separate containers in a single package at least one ingredient selected from the group consisting of antioxidants and mitochondrial cofactors and at least one different ingredient selected from the group consisting of antioxidants and mitochondrial cofactors.

In one embodiment, the kit further comprises one or more food ingredients in a separate package. In this embodiment, the composition or individual composition components are admixed with the food ingredients just prior to administering the resulting admixture to an animal. Generally, the kits contain the composition components in amounts sufficient to supply to an animal at least about 100 ppm of one or more antioxidants and/or at least about 25 ppm of one or more mitochondrial cofactors. In one embodiment, the kit contains at least about 500 ppm vitamin E, at least about 40 ppm vitamin C, at least about 100 ppm L-carnitine, and at least about 25 ppm α-lipoic acid.

In other embodiments, the kits further comprise one or more renal drugs in a separate package.

In other embodiments, the kits further comprise one or more renal diagnostic devices for determining kidney function and evaluating the presence and severity of kidney disease in an animal in a separate package. The renal diagnostic devices useful in the present invention include any device suitable for determining kidney function and evaluating the presence and severity of kidney disease in an animal. Preferred diagnostic methods include serum urea nitrogen (SUN), creatinine levels, urine specific gravity, and DNA damage, including urine assays for albumin such as those described in U.S. Pat. No. 6,589,748, U.S. Pat. No. 6,447,989 and USPAN 20050026225 and comet trail assays. Diagnostic methods are based upon known techniques including (1) blood markers such as elevated blood urea nitrogen concentration, elevated serum creatinine concentration, hyperphosphatemia, hyperkalernia or hypokalemia, metabolic acidosis and hypoalbuminemia, (2) urine markers such as impaired urine concentrating ability, proteinuria, cylinduria, renal hematuria, inappropriate urine pH, inappropriate urine glucose concentration, and cystinuria, (3) physical, imaging, and diagnostic markers such as size, shape, location, and density, (4) single nucleotide polymorphisms (SNPs) such as those disclosed in WO 2004113570 A2, (5) genetic profiles that are indicative of kidney disease, (6) proteomic profiles that are indicative of kidney disease, and (7) metabolic profiles that are indicative of kidney disease. These diagnostic methods and devices (e.g., test strips. ELISA assays, comet assays,) based upon such methods are commonly available to skilled artisans such as scientists and health care professionals and many are available to consumers, e.g., the Heska Corporation's (Fort Collins Colo.) E.R.D.-HealthScreen Urine Tests that detects small amounts of albumin in the urine ("microalbuminuria").

In other embodiments, the kits further comprise information that the use of the compositions and methods of the present invention will prevent or treat kidney disease or improve kidney function.

The kits of the present invention contain the compositions, composition components, food compositions, food ingredients, renal drugs, and renal diagnostic devices in any of various combinations. For example, one kit comprises a food composition comprising an admixture of one or more food ingredients and the composition in combination with a renal diagnostic device or a renal drug or both. Another kit contains the composition components in separate packages and one or more food ingredients in one or more separate packages with or without renal drugs or renal diagnostic devices in separate packages. Numerous such combinations can be constructed by the skilled artisan.

In another aspect, the present invention provides a means for communicating information about or instructions for admixing and administering one or more of the compositions, composition components, food compositions, food ingredients, and renal drugs and information about or instructions for using the renal diagnostic devices of the present invention. The communicating means comprises a document, digital storage media, optical storage media, audio presentation, or visual display containing the information or instructions. Preferably, the communication is a displayed web site or a brochure, product label, package insert, advertisement, or visual display containing such information or instructions. Useful information includes one or more of (1) methods and techniques for combining and administering the compositions, composition components, food compositions, food ingredients, and renal drugs, (2) information for using the renal diagnostic devices, (3) details about the side effects, if any, caused by using the present invention in combination with other drugs, and (4) contact information for animals to use if they have a question about the invention and its use. Useful instructions include dosages, administration amounts and frequency, and administration routes. The communication means is useful for instructing an animal on the benefits of using the present invention and communicating the approved methods for administering the invention to an animal.

The compositions, methods, and kits are useful for decreasing the morbidity and mortality for animals susceptible to or suffering from kidney disease and for improving kidney function, particularly in aging and senior animals.

EXAMPLES

This invention can be further illustrated by the following examples of preferred embodiments thereof, although it will be understood that these examples are included merely for purposes of illustration and are not intended to limit the scope of the invention unless otherwise specifically indicated.

Example 1

Urine samples from 48 senior dogs, all greater than 8 years of age, were first analyzed for albumin content using a microalbuminuria test kit commercially available from Heska Corporation, Fort Collins, Colo. The dogs were then separated into two groups, a control group and a test group, having 24 dogs each. The control group was fed, for a minimum of one year, a food formulated to meet AAFCO recommendations for nutrient intake for adult dogs as their sole nutrition source. The test group was fed, for a minimum of one year, a fortified but otherwise substantially identical, food having enhanced levels of vitamin E, vitamin C, L-carnitine and DL-α-lipoic acid. Additionally, the fortified food contained 1% tomato pomace, 1% dried spinach, 1% dried carrot, 1% dried citrus pulp and 1% dried grape pomace. The ingredients of the control and fortified foods were identical, except as described in Table 1. The tomato pomace, dried spinach, dried carrot, dried citrus pulp and dried grape pomace in the fortified food replaced corn used in the control food.

TABLE 1

Compositions of Control and Fortified Foods

| Ingredient | Control | Fortified |
| --- | --- | --- |
| Vitamin E | about 100 ppm | about 1000 ppm |
| L-carnitine | None added | about 260 ppm |
| DL-α-lipoic acid | None added | about 120 ppm |
| Vitamin C | None added | about 80 ppm |
| Tomato pomace | None added | 1% |
| Dried spinach | None added | 1% |
| Dried carrot | None added | 1% |
| Dried citrus pulp | None added | 1% |
| Dried grape pomace | None added | 1% |

After at least one year, urine samples were taken from each of the dogs and tested for albumin. One dog from the control group was lost to follow-up during the study. If a sample was not available after at least one year, the next available sample was taken either prior to (in cases of dogs that died prior to one year) or after that time point (no more than six months separation).

The Heska microalbuminuria assay tests for presence of albumin at very low concentrations in the urine, and, as noted above, microalbuminuria is considered to be an early indicator of renal glomerular disease. Results are read as categories (none, mild, moderate, severe) against a color scale.

The dogs that were fed the control food, without enhanced levels of antioxidants or mitochondrial cofactors, were more likely to worsen in severity of renal microalbuminuria than the dogs that were fed the test food. A total of 9 animals out of 23 in the control group, but only 5 of 24 animals in the test group worsened in severity. Further, 3 animals in the test group actually exhibited a decrease in severity, whereas only 1 animal in the control group exhibited such a decrease.

Further, as shown in Table 2, fully 50% of the control animals that were in the normal range pre-test tested in a non-normal range post-test, as analyzed using a McNemar test. In the test group, only 23% of the animals testing in the normal range pre-test tested in the non-normal range post-test.

TABLE 2

McNemar Test Results

| | Control group | Test group |
| --- | --- | --- |
| Pre-test | 8 normal | 13 normal |
| | 16 non-normal | 11 non-normal |
| Post-test | 4 normal | 10 normal |
| | 19 non-normal | 14 non-normal |

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. A method for treating kidney disease or for improving kidney function comprising administering to an animal a composition comprising at least 500 ppm vitamin E, at least 100 ppm L-carnitine, at least 25 ppm α-lipoic acid, and at least 40 ppm vitamin C, at least 1% by weight of at least one of tomato pomace, dried spinach, dried carrot, dried citrus pulp, and dried grape pomace and at least one food ingredient, wherein the food ingredient is selected from the group consisting of fats, carbohydrates, proteins, fibers, nutritional balancing agents, and mixtures thereof.

2. The method of claim 1 wherein the composition comprises about 500 to about 1500 ppm vitamin E, about 125 to about 400 ppm L-carnitine, about 25 to about 200 ppm α-lipoic acid, and about 40 to about 150 ppm vitamin C.

3. The method of claim 1 further comprising administering the composition to the animal in conjunction with one or more renal drugs.

4. The method of claim 1 comprising administering the composition to the animal in conjunction with one or more additional food ingredients.

5. The method of claim 4 wherein the one or more additional food ingredients and the composition are administered in a food composition comprising an admixture of the one or more additional food ingredients and the composition.

6. The method of claim 4 further comprising administering the composition to the animal in conjunction with one or more renal drugs.

7. The method of claim 4 wherein the composition is admixed with the one or more additional food ingredients just prior to feeding the mixture to the animal.

8. The method of claim 4 wherein the composition is admixed with the one or more additional food ingredients during the manufacturing process used to prepare a food composition.

9. The method of claim 4 wherein the one or more additional food ingredient are selected from the group consisting of fats, carbohydrates, proteins, fibers, nutritional balancing agents, and mixtures thereof.

10. The method of claim 1 wherein the animal is a senior animal.

11. The method of claim 1 wherein the animal is feline or canine.

12. A kit for administering a kidney disease treating amount or a kidney function improving amount of a composition comprising at least 500 ppm vitamin E, at least 100 ppm L-carnitine, at least 25 ppm α-lipoic acid, and at least 40 ppm vitamin C, at least 1% by weight of at least one of tomato pomace, dried spinach, dried carrot, dried citrus pulp, and dried grape pomace and at least one food ingredient, wherein the food ingredient is selected from the group consisting of fats, carbohydrates, proteins, fibers, nutritional balancing agents, and mixtures thereof to an animal comprising in separate containers in a single package at least one ingredient selected from the composition and at least one different ingredient selected from the composition.

13. The kit of claim 12 further comprising one or more renal drugs.

14. The kit of claim 12 further comprising one or more renal diagnostic devices for determining kidney function and evaluating the presence and severity of kidney disease in an animal.

15. The kit of claim 12 further comprising one or more additional food ingredients.

16. The kit of claim 15 further comprising one or more renal drugs.

17. The kit of claim 15 further comprising one or more renal diagnostic devices for determining kidney function and evaluating the presence and severity of kidney disease in an animal.

18. The kit of claim 12 further comprising information that the use of the composition will treat kidney disease.

* * * * *